United States Patent [19]

Cooper, Jr. et al.

[11] 4,325,026
[45] Apr. 13, 1982

[54] PLURAL COIL EDDY CURRENT MAPPING PROBE

[75] Inventors: Frank W. Cooper, Jr., Monroeville; Leonard R. Golick, Trafford, both of Pa.

[73] Assignee: Westinghouse Electric Corp., Pittsburgh, Pa.

[21] Appl. No.: 21,652

[22] Filed: Mar. 19, 1979

[51] Int. Cl.³ .................. G01R 33/12; G01N 27/90
[52] U.S. Cl. .................. 324/232; 324/219; 324/238
[58] Field of Search .................. 324/219–221, 324/228, 229, 232, 234–238

[56] References Cited

U.S. PATENT DOCUMENTS

| | | | |
|---|---|---|---|
| 2,103,256 | 12/1937 | Greenslade | 324/219 |
| 2,104,643 | 1/1938 | Greenslade | 324/219 |
| 2,104,646 | 1/1938 | Greenslade | 324/219 |
| 2,782,365 | 2/1957 | Castel | 324/221 |
| 3,004,215 | 10/1961 | Datt et al. | 324/220 |
| 3,050,678 | 8/1962 | Datt | 324/238 |
| 3,401,332 | 9/1968 | McClurg et al. | 324/232 |
| 3,417,325 | 12/1968 | McCullough et al. | |
| 3,543,144 | 11/1970 | Walters et al. | 324/221 |
| 3,611,119 | 10/1971 | Madewell et al. | 324/228 |
| 3,693,075 | 9/1972 | Forster | |
| 3,916,302 | 10/1975 | Madewell | 324/220 |
| 4,095,181 | 6/1978 | Harris et al. | 324/238 |
| 4,107,605 | 8/1978 | Hudgell | 324/220 |
| 4,204,159 | 5/1980 | Sarian et al. | 324/232 |

FOREIGN PATENT DOCUMENTS

| | | |
|---|---|---|
| 1004387 | 3/1957 | Fed. Rep. of Germany . |
| 2626060 | 2/1977 | Fed. Rep. of Germany ...... 324/220 |

*Primary Examiner*—Gerard R. Strecker
*Attorney, Agent, or Firm*—Daniel C. Abeles

[57] ABSTRACT

An eddy current probe for mapping holes within a tube sheet of a steam generator, having a first coil (12) positioned at the top of the probe (10) with its axis coincident with the axis of the probe. A first coil pair (14 and 16) is arranged along a common axis perpendicular to the axis of the probe below the first coil (12) and is situated a distance from and on either side of the axis of the probe. A second pair of eddy current coils (18 and 20) is positioned along a common axis perpendicular to the axis of the probe and the axis of the first coil pair with the respective coils of the second pair located on either side of and spaced from the probe axis. Each of the respective coils are arranged to be separately excited by an alternating current source with the respective coil pairs coupled in opposition in corresponding balanced bridge arrangements. Means are provided for indicating a variation in the impedance of the first coil and an imbalance in either of the separate bridge arrangements of the first and second coil pairs.

9 Claims, 4 Drawing Figures

U.S. Patent
Apr. 13, 1982
4,325,026
FIG.1.
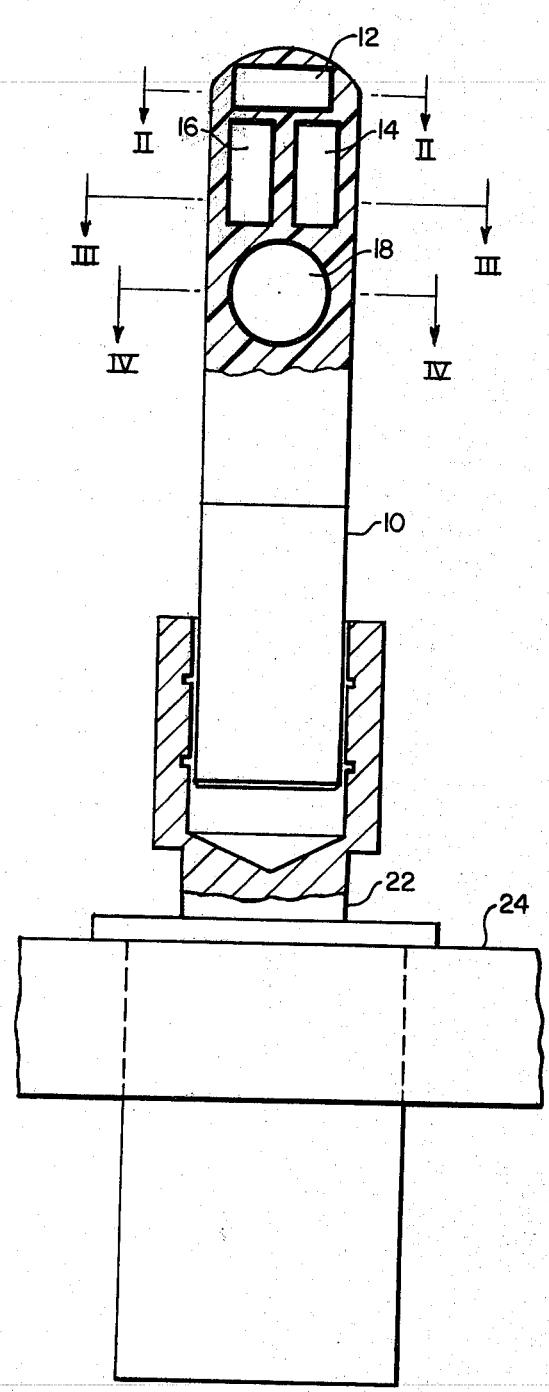
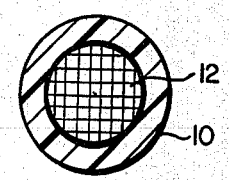
FIG.2.
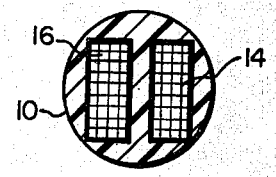
FIG.3.
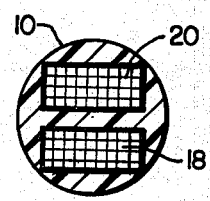
FIG.4.

4,325,026

PLURAL COIL EDDY CURRENT MAPPING PROBE

CROSS-REFERENCE TO RELATED APPLICATIONS

This application is hereby cross-referenced to the following commonly assigned United States patent applications:

U.S. Pat. No. 4,205,940, issued June 3, 1980 entitled "Apparatus for Remotely Repairing Tubes in a Steam Generator";

Application Ser. No. 952,430, filed on Oct. 18, 1978, in the names of Kenneth S. Gerkey, Raymond P. Castner, and Richard L. Stiller, entitled "Heat Exchanger Tube and Tube Sheet Location Sensing Device and Method of Operating Same"; and Application Ser. No. 952,431, filed on Oct. 18, 1978, in the names of Raymond P. Castner and F. W. Cooper, Jr., entitled "Method and Apparatus for Servicing a Steam Generator."

BACKGROUND OF THE INVENTION

1. Field of the Invention

This invention relates to a method and apparatus for servicing a heat exchanger and, more particularly, to a method and apparatus for remotely mapping a tube sheet of such a heat exchanger.

2. Description of the Prior Art

In a pressurized water nuclear-powered electric generating system the heat generated by the nuclear reaction is transferred by a primary coolant that circulates through the reactor core to a steam generator where it is utilized to generate steam. The steam generator typically is an upright cylindrical pressure vessel with hemispherical end sections. A transverse plate called a tube sheet, located at the lower end of the cylindrical section, divides the steam generator into a primary side, which is the lower hemispherical section below the tube sheet, and a secondary side above the tube sheet. A vertical wall bisects the primary side into an inlet section and an outlet section. The tube sheet is a thick carbon steel plate with an array of hundreds of holes into which are inserted the ends of U-shaped tubes. One end of each U-shaped tube is inserted into a hole in the tube sheet which communicates with the inlet section of the primary side, and the other is inserted into a corresponding hole which communicates with the outlet section. The primary coolant is introduced under pressure into the inlet section of the primary side, circulates through the U-shaped tubes and exits through the outlet section. Water introduced into the secondary side of the steam generator circulates around the U-shaped tubes and is transformed into steam by the heat emanating from the primary coolant.

Occasionally, during operation of the steam generator leaks develop in some of the tubes. This is undesirable because the primary coolant can contain some radioactive contamination and any cross-feed of the reactor coolant into the secondary side of the generator, therefore, can contaminate the steam. It is not practical, however, to replace leaky tubing as it occurs, but instead the effected tubes are usually plugged at both ends. In view of the hundreds of tubes in a steam generator, plugging of a few does not appreciably effect the efficiency of heat transfer.

Eventually, however, in some cases, a sufficient number of tubes can become plugged to adversely effect heat transfer. In such cases, it may be desirable to either replace or retube the steam generator. In the retubing process, all the tube holes, including any plugged holes, are drilled out and spot-faced from the primary side, and the tubes are then pulled out from the secondary side. New tubes are inserted from the secondary side with tubing guides inserted in the tube ends to ease their passages through holes in transfer support plates and the tube sheet. The tube guides are then removed from the primary side and the ends of the tubes are aligned with the spot-faced end of the hole in the tube sheet, tack-rolled and then welded in place.

While space to maneuver is not a particular problem on the secondary side of the steam generator, the radius of the partitioned, hemispherical primary side is typically approximately 5 feet, which does not provide much working room, especially near the circumference of the tube sheet. In addition, the primary side is usually radioactive, which requires worker protection and limitation of exposure.

In order to minimize worker exposure, a computerized, automated manipulator has been designed to carry out most of the tooling operations required on the primary side. As described in patent application Ser. No. 952,431, filed Oct. 18, 1978, the automated manipulator is capable of positioning the required tooling at almost any location on the primary side of the tube sheet to effect the desired machining processes. However, experience has shown that the location of the tube sheet holes will vary from generator to generator. Accordingly, it is desirable to map the holes in each tube sheet prior to performing the tooling operations required in retubing a steam generator so that the remote manipulator can properly position its end-affecters to carry out the necessary operations.

Therefore, a mapping end-effector is desired that can precisely locate the center line of each hole in the primary side of the tube sheet. Furthermore, it is desirable that such a probe identify whether or not each hole mapped is plugged and the nature of the plugs. Additionally, it is desirable to have such a tool that can indicate the diameter of each of the holes to be mapped.

SUMMARY OF THE INVENTION

According to the invention, an eddy current probe is provided for mapping holes which extend into and at least partially through a magnetic material. The probe is contained within a housing sized to be slidably inserted into the holes to be mapped, in a direction parallel to a given axis of the probe. A first eddy current coil is affixed at one end of the probe, having its axis of revolution parallel to the given axis of the probe. A second eddy current coil is positioned within the housing on one side of and having its axis of revolution perpendicular to the given axis of the probe. A third eddy current coil, situated in juxtaposition to and along a common axis of revolution with the second eddy current coil, is positioned within the housing on the opposite side of the given axis of the probe. A fourth eddy current coil is positioned within the housing on one side of the given axis of the probe, having its axis of revolution perpendicular to the given axis of the probe and the axis of revolution of the second and third eddy current coils. A fifth eddy current coil is positioned within the housing in juxtaposition to and along a common axis of revolution with the fourth eddy current coil, on the opposite side of the given axis of the probe. Means are provided for communicating an alternating current to excite the respective coils, and means are supplied for providing an electrical output representative of the relative impedance of the respective coils.

In accordance with this invention, the eddy current probe is placed adjacent to and orientated so that its given axis is substantially perpendicular to the surface being monitored so that the eddy current generated by the first coil has a path through the surface. As the probe is scanned across the surface the impedance of the first coil is monitored to determine the general location of holes within the surface. The probe is then inserted into each hole and maneuvered until the relative impedance of the second and third coils and fourth and fifth coils are balanced. The exact location of the center line of the hole can then be noted from the probe's position. In the preferred embodiment the monitored impedance of the first coil provides an indication of the diameter of each hole scanned, whether nor not the hole is plugged and the nature of the plug.

BRIEF DESCRIPTION OF THE DRAWINGS

For a better understanding of the invention, reference may be had to the preferred embodiment, exemplary of the invention, as shown in the accompanying drawings, in which:

FIG. 1 is a perspective view of the probe of this invention, with portions thereof cut away for clarity;

FIG. 2 is a cross-sectional view of the probe of FIG. 1 taken along the lines II—II thereof;

FIG. 3 is a cross-sectional view of the probe of FIG. 1 taken along the lines III—III thereof; and, FIG. 4 is a cross-sectional view of the probe of FIG. 1 taken along the lines IV—IV thereof.

DESCRIPTION OF THE PREFERRED EMBODIMENT

As described in application Ser. No. 952,431, filed Oct. 18, 1978, in the process of retubing a steam generator it is desirable to map the tube sheet with a probe to obtain and store information on the precise location and condition of each hole. The stored locations are then used to maneuver various tools into position to perform one or more operations at each tube hole. The probe for precisely performing this task and its method of operation is a subject of this invention.

The preferred embodiment of the probe of this invention is illustrated in FIG. 1 which shows an elongated probe housing 10 constructed from fiberglass and epoxy which serves as a coil and lead wire holder. The probe housing 10 is fitted into an intermediate socket 22 which in turn couples into the manipulator arm socket 24. The manipulator is more fully described in the aforecited applications. The eddy current coils 12, 14, 16, 18 and 20 form the active components of the probe.

Referring to FIG. 2, it can be appreciated that coil 12 is wound about the central longitudinal axis of the probe and when positioned adjacent to the tube sheet surface and excited by a corresponding alternating current source, will generate an eddy current having a path through the tube sheet surface being mapped. The coil 12 has two external leads which, though not shown, run through the longitudinal length of the housing and into the remote manipulator fixture through which it is coupled to the alternating current source. A means for measuring the impedance of the coil, such as an ammeter, is connected in the coil circuit to provide an indication of the effect of dicontinuities in the surface being mapped in the eddy current path. In operation, the probe is orientated to have its longitudinal axis perpendicular to the surface of the tube sheet while it is scanned across the surface. Discontinuities in the impedance readings in the circuit of the coil 12 provide an indication of the presence and diameter of holes in the surface adjacent the probe. In addition, the nature of the discontinuities can be interpreted to identify whether or not the individual holes are plugged, and if sealed, the nature of the seal.

Two additional coils 14 and 16 are situated in juxtaposition on either side of, and having their axis of revolution perpendicular to, the longitudinal axis of the probe. Coils 18 and 20 are similarly situated in juxtaposition on either side of and perpendicular to the longitudinal axis of the probe, and are additionally orientated perpendicular to the axis of revolution of coils 14 and 16. The orientation of coils 14, 16, 18 and 20 can better be appreciated by reference to FIGS. 3 and 4. Coils 14 and 16, like coil 12, have external leads through which they are each coupled to an alternating current source and connected in opposition to an electrical impedance bridge arrangement with means, such as an ammeter, inserted in the circuit arrangement to provide an indication of an electrical imbalance in the bridge circuit. Similarly, coils 18 and 20 are connected in the same manner in an electrical bridge arrangement so that a change in the corresponding eddy current path of one coil in either of the two coil pairs, which is not reproduced in the eddy current path of the other coil within the same pair, will provide an imbalance which will be indicated by the impedance measuring device.

In operation, once a hole is identified by coil 12, the probe is inserted into the hole and maneuvered so that the imbalances in the coils of the two coil pairs are minimized. The hole's center line is identified from the probe's position at which a minimum imbalance is achieved. The hole's precise location is then stored within the memory of the manipulator controls, for future reference during the tooling operation.

In the preferred embodiment, coils 14 and 16 are sized larger than coil 12 to produce an enlarged eddy current field which serves to columnate and focus the eddy current path generated by coil 12. Desirably, the coils are shielded from one another by the use of ferrite material and by the proper balancing of the electrical energizing signals.

In this manner, the coarse mapping provided by coil 12 can identify the rough center line of a hole within 0.020" of true position, and insertion of the probe within the hole and manipulation of the probe to null the bridge arrangements of coils 14 and 16 and 18 and 20 can establish the center line within 0.001" of true position. In addition, coil 12 can be calibrated to determine the mean hole diameter within 0.002".

What is claimed is:

1. An eddy current probe for mapping holes which extend into and at least partially through a magnetic material comprising:

a probe housing sized to be slidably inserted into the holes to be mapped in a direction parallel to a given axis of the probe;

a first eddy current coil affixed at one end of the probe having its axis of revolution parallel to the given axis of the probe;

a second eddy current coil positioned on one side of and having its axis of revolution perpendicular to the given axis of the probe;

a third eddy current coil situated in juxtaposition to and along a common axis of revolution with the second eddy current coil on the opposite side of the given axis of the probe;

a fourth eddy current coil positioned on one side of and having its axis of revolution perpendicular to the given axis of the probe and perpendicular to the axis of revolution of the second and third eddy current coils;

a fifth eddy current coil positioned in juxtaposition to and along a common axis of revolution with the fourth eddy current coil on the opposite side of the given axis of the probe;

means for communicating an alternating current to excite the respective coils; and means for providing an electrical output representative of the relative impedance of the respective coils.

2. The eddy current probe of claim 1 wherein the second and third eddy current coils are spaced along the given axis of the probe from the fourth and fifth eddy current coils.

3. The eddy current probe of claim 2 wherein the first eddy current coil is spaced along the given axis of the probe from the second and third eddy current coils.

4. The eddy current probe of claim 1 wherein each of the coils is directly excited from an alternating current source.

5. The eddy current probe of claim 1 wherein the second and third eddy current coils are connected in opposition in an electrical bridge arrangement.

6. The eddy current probe of claim 5 wherein the fourth and fifth eddy current coils are connected in opposition in an electrical bridge arrangement.

7. The eddy current probe of claim 5 wherein the second and third eddy current coils are impedance-matched.

8. The eddy current probe of claim 1 including magnetic shielding between the respective coils.

9. The eddy current probe of claim 1 wherein the second and third eddy current coils are arranged to columnate the eddy current path generated by the first coil.

* * * * *